United States Patent [19]
Grain et al.

[11] Patent Number: 4,766,223
[45] Date of Patent: Aug. 23, 1988

[54] PREPARATION OF 2-ALKYL-3-(4-HYDROXYBENZOYL)BENZOFURAN

[75] Inventors: Claude Grain, Volonne; Fernand Jammot, Sisteron, both of France

[73] Assignee: Sanofi, Paris, France

[21] Appl. No.: 876,003

[22] Filed: Jun. 19, 1986

[30] Foreign Application Priority Data

Jun. 25, 1985 [FR] France ............... 85 09669

[51] Int. Cl.$^4$ ........................... C07D 307/80
[52] U.S. Cl. .................. 549/468; 549/210
[58] Field of Search .......... 549/468, 206, 210

[56] References Cited

U.S. PATENT DOCUMENTS 3,331,854 7/1967 Huffman et al. ............... 549/468
3,426,124 2/1969 Baron et al. ............... 549/468

FOREIGN PATENT DOCUMENTS 1260578 4/1961 France .
1339389 8/1963 France .
175906 3/1981 Hungary .

OTHER PUBLICATIONS

R. Royer et al, Bull. Soc. Chim. France (1960) pp. 685–688.
M. Haring et al, Helvetica Chimica Acta, vol. 37 (1954) (1), pp. 147–154.
B. P. Susz et al, Helvetica Chimica Acta, vol. 37 (4) (1954), pp. 1273–1280.
B. P. Susz et al, Helvetica Chimica Acta, vol. 41 (5) (1958), pp. 1332–1341.
George A. Olah, Friedel–Crafts and Related Reactions, vol. III, Part 1, (1964), pp. 8–11, 83–84.
George A. Olah, Friedel–Crafts and Related Reactions, vol. IV (1965), pp. 5–6, and 225.
W. Baker, Jour. Chem. Soc., (1941), pp. 662–672.
Chem. Ab. 92, 1980, (215179a).
Chem. Ab. 94, 1981 (192122b).
B. P. Susz et al, Helvetica Chimica ACTA, vol. XLI, (1958), pp. 1332–1341.
Starowieyski et al, "Complexes of Carbonyl Compounds with $R_nAlX_{3-n}$Compounds", Journal of Organometallic Chemistry, 94(1975) 361–366.

Primary Examiner—Norma S. Milestone
Attorney, Agent, or Firm—Bacon & Thomas

[57] ABSTRACT

The invention relates to new molecular complexes of general formula:

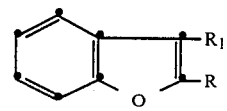

in which R represents a straight- or branched-chain alkyl radical having from 1 to 4 carbon atoms and $R_1$ represents one of the radicals:

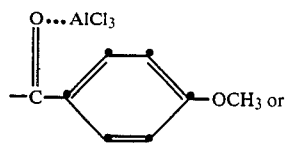

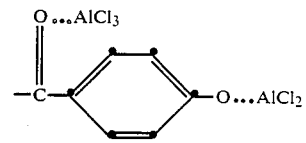

These molecular complexes are especially useful for the preparation of 2-alkyl-3-(4-hydroxybenzoyl)benzofurans.

6 Claims, No Drawings

PREPARATION OF 2-ALKYL-3-(4-HYDROXYBENZOYL)BENZOFURAN

The present invention relates, in a general manner, to new molecular complexes composed of a benzofuran derivative and of aluminum chloride, to their preparation and to their use.

The molecular complexes of the invention correspond to the general formula:

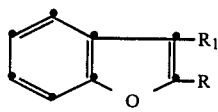

in which R represents an alkyl radical and $R_1$ represents one of the radicals:

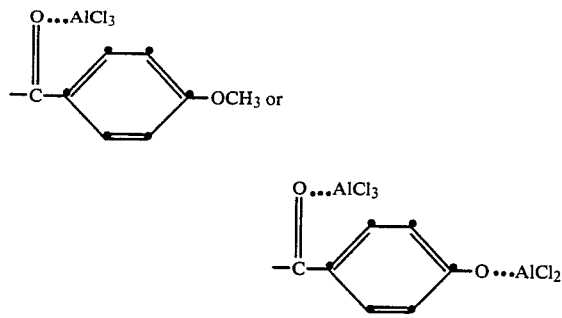

In the present context, "alkyl radical" means a straight- or branched- and saturated hydrocarbon radical containing from 1 to 4 carbon atoms, more especially an ethyl or n-butyl radical.

The complexes of formula I may be used widely as synthesis intermediates, especially for the final synthesis of the benzofuran derivatives described in French patent Nos. 1,260,578 and 1,339,389. Such derivatives are, in particular: benzarone or 2-ethyl-3-(4-hydroxybenzoyl)benzofuran, benziodarone or 2-ethyl-3-(3,5-diiodo-4-hydroxybenzoyl)benzofuran, benzbromarone or 2-ethyl-3-(3,5-dibromo-4-hydroxybenzoyl)benzofuran and amiodarone or 2-n-butyl-3-(3,5-diiodo-4β-diethylaminoethoxy benzoyl)benzofuran.

These complexes have been found to be of special interest because of their therapeutic applications. Thus, benzarone has been found useful because of its phlebotonic and retardant action in capillaroveinous inflammatory reactions, benziodarone because of its coronarodilatant and hypouricemiant activity, benzbromarone because of its hypouricemiant action and amiodarone because of its cardiac antianginal and antiarrhythmic properties.

Consequently, a first object of the invention relates to the molecular complexes of formula I, as new industrial products which are useful especially as intermediates, for example for the final synthesis of benzarone, benziodarone, benzbromarone and amiodarone.

It is known that Lewis bases such as ketones, ethers and amides can form molecular complexes with Lewis acids such as titanium, iron or aluminium chlorides.

Complexes which are more or less stable, for example of the type $>C=O...AlCl_3$ have occasionally been isolated and studied in the solid state, despite their considerable instability and hygroscopicity.

The composition of these complexes can vary according to the conditions under which they are prepared and the molar ratios of base to acid.

Examples of such complexes formed, on the one hand, between benzophenone or acetophenone and, on the other hand, aluminium chloride have been described in Helv. Chim. Acta, 1954, vol. XXXVII IV, 147 1273 and 1958, vol. XLI V, 146, 1333. However, no molecular complex formed by a benzofuran derivative and a Lewis acid especially aluminium chloride, has been reported until now.

It is known, furthermore, that anhydrous aluminium chloride is completely insoluble in aromatic hydrocarbons such as benzene or toluene.

However, it has been observed within the scope of the present invention, that this substance dissolves virtually instantly at a temperature below or equal to 40° C. in toluene or benzene solutions of a 2-alkyl-3-(4-methoxy-benzoyl)benzofuran.

This "dissolution" is associated with a high exothermicity and can be observed for aluminium chloride/2-alkyl-3-(4-methoxybenzoyl)benzofuran molar ratios of up to 2.6.

It has therefore been postulated that this dissolution of aluminium chloride in such aromatic hydrocarbon solutions could be due to the formation of one or more molecular complexes of aluminium chloride with the 2-alkyl-3-(4-methoxybenzoyl)benzofuran.

As a result, spectroscopic studies have been undertaken in order to verify this hypothesis and to define the presumed interaction between the 2-alkyl-3-(4-methoxybenzoyl)benzofuran and aluminum chloride.

As an example, the following results were obtained for aluminium chloride and 2-n-butyl-3-(4-methoxybenzoyl)benzofuran.

Ternary solutions composed of aluminium chloride, 2-n-butyl-3-(4-methoxybenzoyl)benzofuran and deuterated benzene were prepared, and the molar ratio:

$$r = \frac{\text{aluminium chloride}}{\text{2-n-butyl-3-(4-methoxybenzoyl)benzofuran}}$$

has been varied from 0 to 3.

Thus, it has been possible to demonstrate the following:

A. By means of N.M.R. (nuclear magnetic resonance) spectroscopy, the absence of change in the —OCH$_3$ group between molar ratios of 0 and 1 ($\delta = 3.2$ ppm) and an increase by +0.35 ppm in chemical shift between the ratios 1 and 3, which may correspond to an ether-AlCl$_3$ interaction.

B. By means of I.R. (infrared) spectroscopy, the virtual absence of changes in the characteristic absorptions of the C—O—C groups in the region 1200-1000 cm$^{-1}$, in this case the C—O—C group in benzofuran. I.R. spectroscopy has also shown the disappearance of the "free" C=O$\nu$ band at 1654 cm$^{-1}$ of 2-n-butyl-3-(4-methoxybenzoyl)benzofuran and the appearance of a band situated at 1545 cm$^{-1}$ ("associated" C=O$\nu$ band) in toluene, for molar ratios ranging from 0 to 1.5 and when aluminium chloride is added. The drop in frequency by 100 cm$^{-1}$ is indicative of strong complexing. The virtually complete disappearance of the free band at a molar ratio r=1 shows that, at this stage, all of the 2-n-butyl-3-(4-methoxybenzoyl) benzofuran is involved in a complex with aluminium chloride, and that the latter is probably of the 1:1 type and involves the ketone site. This molecular complex could thus appear to correspond to the formula:

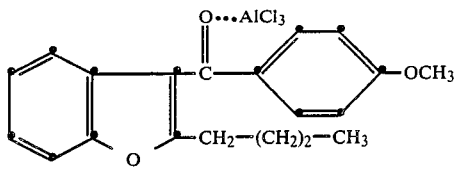

The 1:1 complex defined in this manner has been successfully isolated from methylene chloride solutions.

It exists in the form of a poorly-crystallized yellow solid. The complex appears to be stable when stored in the absence of moisture at a low temperature ($\leq 20°$ C.). It melts with decomposition between 25° and 40° C.

The I.R. spectrum of the 1:1 molecular complex in question, obtained by operating very rapidly to avoid hydrolysis (suspension in liquid paraffin), shows, when compared to the spectrum of a film of 2-n-butyl-3-(4-methoxybenzoyl)benzofuran, the disappearance of the "free" C=O$\nu$ band. The "associated" C=O$\nu$ band appears broad and poorly defined between 1500 and 1550 cm$^{-1}$.

After the 1:1 complex has been dissolved in toluene or benzene, its I.R. and N.M.R. spectra show very precisely the spectral perturbations observed in the course of the investigation of the ternary solutions for the molar ratio r=1, the results of which were reported hereabove.

The results of spectroscopic studies of ternary solutions have also made it possible to postulate the formation of a molecular complex between aluminium chloride and 2-n-butyl-3-(4-methoxybenzoyl)benzofuran in the molar ratio 2:1. However, the fact that a 2:1 complex is involved has not been proved.

On the other hand, it has also been possible to demonstrate that toluene solutions containing aluminium chloride and 2-n-butyl-3-(4-methoxybenzoyl)benzofuran in a ratio of r=2 give rise to a new complex after these solutions have been added to an aromatic hydrocarbon, for example benzene or toluene, which is kept under reflux. This new complex, which corresponds to a demethylation complex, corresponds to the formula:

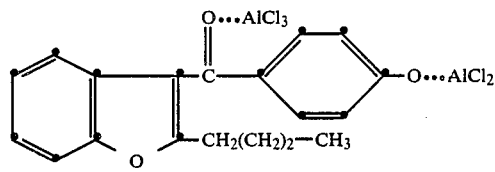

It exists in the form of a finely-divided yellowish powder melting with decomposition above 300° C.

In conclusion, it can be confirmed that an interaction takes place between the ketonic group of a 2-alkyl-3-(4-methoxybenzoyl)benzofuran and aluminium chloride at a low temperature ($\leq 20°$ C.) in an aromatic hydrocarbon such as benzene or toluene and that this takes place at aluminium chloride/2-alkyl-3-(4-methoxybenzoyl)-benzofuran molar ratios of up to 2, that there is no interaction with the C—O—C group in benzofuran, and that a weak interaction appears to occur with the ether group only beyond a ratio of 1.

It can therefore be assumed that the hypothetical 2:1 complex of aluminium chloride with 2-alkyl-3-(4-methoxybenzoyl)benzofuran, which would appear to form in the cold (temperature $\leq 20°$ C.) in an aromatic hydrocarbon such as benzene or toluene, would appear to undergo a thermal modification with migration of one molecule of aluminium chloride from the ketone group to the ether group of the 2-alkyl-3-(4-methoxybenzoyl)benzofuran, to permit the demethylation.

Another object of the invention relates to a process for preparing the 1:1 molecular complexes of formula I in which R$_1$ represents the radical

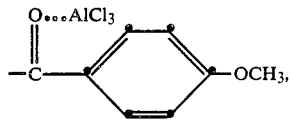

process which comprises reacting aluminium chloride and the 2-alkyl-3-(4-methoxybenzoyl)benzofuran in a ratio of 1 to 2:1, in an aromatic hydrocarbon medium such as, for example, toluene or benzene, or in a chloroalkane medium such as dichloromethane, and at a temperature below or equal to room-temperature, to obtain the 1:1 complex of aluminium chloride with 2-alkyl-3-(4-methoxybenzoyl)benzofuran.

Similarly, the invention relates to a process for preparing the 2:1 molecular complexes of formula I in which R$_1$ represents the radical

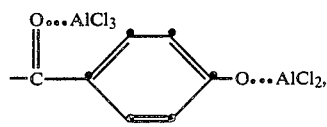

which comprises heating under reflux, a solution containing the 1:1 complex according to the invention, i.e. a solution made up initially of 1 to 2 mols of aluminium chloride per mol of 2-alkyl-3-(4-methoxybenzoyl)benzofuran and of an aromatic hydrocarbon such as benzene or toluene as a solvent, to produce the 2:1 complex of aluminium chloride with 2-alkyl-3-(4-hydroxybenzoyl)benzofuran.

According to a preferred embodiment, a solution of 1 to 2 mols of aluminium chloride per mol of 2-alkyl-3-(4-methoxybenzoyl)benzofuran in an aromatic hydrocarbon is produced at a temperature below or equal to room-temperature. The solution obtained in this manner, which contains the 1:1 complex of aluminium chloride with 2-alkyl-3-(4-methoxybenzoyl)-benzofuran according to the invention is then poured into an aromtic hydrocarbon heated to reflux, so as to form the 2:1 complex of aluminium chloride with 2-alkyl-3-(4-hydroxybenzoyl)benzofuran according to the invention.

The invention also relates to a solution containing the molecular complexes of the invention and suitable, in particular, as a reaction medium for producing the demethylation of the ether group of a 2-alkyl-3-(4-methoxybenzoyl)benzofuran, a solution initially made up of 1 to 2 mols of aluminium chloride per mol of 2-alkyl-3-(4-methoxybenzoyl)-benzofuran and of an aromatic hydrocarbon such as benzene or toluene, as solvent.

At a temperature below or equal to room-temperature, this solution contains the 1:1 complex according to the invention and, at the reflux temperature, the 2:1 complex of the invention.

The starting 2-alkyl-3-(4-methoxybenzoyl)benzofurans are known products which may be prepared, for example, according to the process described in Bull. Soc. Chim. France pp. 685–688 (1960) or in French patent No. 1,260,578, by condensing, in accordance with the Friedel-Crafts reaction, a 2-alkylbenzofuran and 4-methoxybenzoyl chloride in benzene, at a temperature of between 0° C. and room-temperature, and in the presence of stannic chloride as a catalyst, followed by hydrolysis in the presence of a strong acid such as hydrochloric acid.

According to a preferred method, the 2-alkyl-3-(4-methoxybenzoyl) benzofuran is prepared at a temperature of between −10° C. and room-temperature, also using the Friedel-Crafts reaction, from the 2-alkyl benzofuran, a 4-methoxybenzoyl halide preferably the chloride, an aromatic hydrocarbon as a solvent, for example benzene or, preferably, toluene, and in the presence of a catalyst, with subsequent hydrolysis in the presence of a strong acid, for example hydrochloric acid. In this variant, however, ferric chloride is used as a catalyst.

It has been observed, in fact, that this compound produces results which are better than those given by other Lewis acids such as aluminium chloride, zinc chloride, boron trifluoride etherate or stannic chloride. Compared to the last-mentioned, the advantages offered by ferric chloride may be summarized as follows:

complete charging of ferric chloride into the reactor, in a single operation. This is reflected in a saving in manpower when compared to the known process which, in fact, requires several hours for the addition of stannic chloride;

a cost reduction, on the one hand because of the use of ferric chloride instead of stannic chloride and, on the other hand, because of a 90% reduction in the quantity of strong acid used in the hydrolysis;

a gain in yield, due to the fact that the 2-alkyl-3-(4-methoxybenzoyl)benzofuran can be used in a crude state to produce the molecular complexes of the invention;

increased safety of the personnel, as a result of the use of ferric chloride, which is less toxic than stannic chloride;

a reduction in the content of isomers of 2-alkyl-3-(4-methoxybenzoyl)benzofuran (products of acylation in positions 5 and 6 of the homocyclic ring) as the yield increases. For example, in the preparation of 2-n-butyl-3-(4-methoxybenzoyl)benzofuran, the process requiring the use of stannic chloride gives rise to approximately 5% of isomers, whereas the method which employs ferric chloride gives at most 2% of these isomers.

Such an advantage is of particular interest, because it avoids the difficult purification of the 2-alkyl-3-(4-methoxybenzoyl)benzofuran in the form of oils.

Surprisingly, in the present case ferric chloride has been found to be more selective than stannic chloride, while affording yields which are practically quantitative.

The isomers of 2-n-butyl-3-(4-methoxybenzoyl)benzofuran, just discussed, have been isolated and their structure has been determined by N.M.R. (nuclear magnetic resonance) spectroscopy of $^{13}C$.

The material in question is a mixture of 2-n-butyl-6-(4-methoxybenzoyl)-benzofuran and 2-n-butyl-5-(4-methoxybenzoyl)benzofuran in proportions of approximately 85:15.

Unless they are removed, these impurities take part in the subsequent reactions in which 2-n-butyl-3-(4-methoxybenzoyl)benzofuran is used and will initially lead, for example, to the corresponding isomers of 2-n-butyl-3-(4-hydroxybenzoyl)benzofuran, and then, in turn, to the corresponding isomers of amiodarone.

The 2:1 molecular complexes of the invention may be used in order to prepare 2-alkyl-3-(4-hydroxybenzoyl)-benzofuran.

Consequently, another object of the invention relates to the use of the 2:1 molecular complexes of the invention to prepare, by demethylation, 2-alkyl-3-(4-hydroxybenzoyl)benzofurans, for instance in a process according to which a solution of the complexes in question in an aromatic hydrocarbon such as benzene or, preferably, toluene, as a solvent, is kept under reflux, and then hydrolysis is carried out in the presence of a strong acid, for example hydrochloric acid, at a temperature of the order of 75° to 80° C.

The solution of the 2:1 molecular complex of the invention may consist:

either of an extemporaneous solution of the 2:1 complex in question in the chosen solvent, or of a solution of aluminium chloride and of 2-alkyl-3-(4-methoxybenzoyl)benzofuran in a molar ratio of 1 to 2:1, also in the chosen solvent. In this case, the aluminium chloride/2-alkyl-3-(4-methoxybenzoyl)benzofuran solution in question may itself be prepared:

either by adding anhydrous aluminium chloride and 2-alkyl-3-(4-methoxybenzoyl)benzofuran, isolated beforehand from the medium of its preparation, to the chosen solvent;

or by addition of anhydrous aluminium chloride to a solution of 2-alkyl-3-(4-methoxybenzoyl)benzofuran in the crude state, that is to say not isolated from its preparation medium.

Various ways of using the reactants which are required for preparing the solution of the 2:1 complex according to the invention and, lastly, for the demethylation reaction, have been tested, namely:

charging all the reactants at room-temperature and heating to reflux. This method of implementation, which can be applied in the laboratory, turns out to be dangerous on an industrial scale because of the risk of a runaway reaction, either because of the exothermicity of the latter, or because of an excessively violent release of the methyl chloride formed;

addition of aluminium chloride to the aromatic hydrocarbon, heating to reflux and gradual running-in of the solution of 2-alkyl-3-(4-methoxybenzoyl)benzofuran, while reflux is maintained.

A disadvantage of this variant is that a very large excess of aluminium chloride is maintained in the reaction medium, in relation to the benzofuran derivative during the entire running-in period, and this can result in a partial deacylation of the 2-alkyl-3-(4-methoxybenzoyl)benzofuran.

On the other hand, it has been found that the demethylation in question may be effected very easily by using a method which is quite special.

Thus, according to the invention, a solution of 1 to 2 mols of aluminium chloride per mol of 2-alkyl-3-(4-methoxybenzoyl)benzofuran in the chosen aromatic hydrocarbon is made up at a temperature below or equal to room-temperature, so as to form the 1:1 complex of aluminium chloride with 2-alkyl-3-(4-methoxybenzoyl)benzofuran of the invention, and the solution obtained, for example a solution containing approximately 30% of this complex, is poured into the solvent in question, maintained under reflux, which causes the formation of the 2:1 complex of aluminium chloride with 2-alkyl-3-(4-hydroxybenzoyl)benzofuran of the invention.

The hydrolysis of the 2:1 complex solution formed in this manner is then carried out as indicated above, namely in the presence of a strong acid at a temperature not exceeding 75° C. to 80° C.

According to a known method for effecting the demethylation of 2-n-butyl-3-(4-methoxybenzoyl)benzofuran, this compound is heated to 210° C. -220° C. in the presence of pyridine hydrochloride, and hydrolysis is carried out in the presence of hydrochloric acid, as described in French patent No. 1,260,578.

Compared to this known method, the demethylation of 2-alkyl-3-(4-methoxybenzoyl)benzofuran using the molecular complexes of the invention offers a number of advantages, among which it is possible to mention:

a lower operating temperature than that of the known process. As a result of this, the synthesis may be carried out in a conventional apparatus making it possible, for example, to perform the refluxing of toluene at atmospheric pressure (110° C.) or under reduced pressure (80° C.), while avoiding the use of a heat transfer fluid as a heating medium to obtain the temperature conditions of the prior process;

elimination of the use of toxic pyridine, thereby ensuring increased safety of the personnel;

improved yield and quality;

absence of the impurity present in a proportion of 3 to 10% in the previous process, depending on the water content of the reaction medium. In the case of the demethylation of 2-ethyl-3-4-methoxy)benzyolfuran, this impurity corresponds to 2-(4-hydroxyphenyl)-3-propionyl-benzofuran (m.p. : 171° C.), and in the case of 2-n-butyl-3-(4-methoxybenzoyl)benzofuran it is more likely to be a deacylation product, namely 2-(4-hydroxyphenyl)benzofuran (m.p.: 196° C.; I.R. spectrum: absence of a C=O $\nu$ band, presence of an OH band; N.M.R. spectrum: absence of n-$C_4H_9$).

The presence of such impurities is particularly awkward. In fact, they require at least one double purification of the 2-alkyl-3-(4-hydroxybenzoyl) benzofuran without the possibility of recycling mother-liquors. Since, in general, these impurities are more insoluble than the 2-alkyl-3-(4-hydroxybenzoyl)benzofuran in the usual solvents, their removal is found to be particularly difficult.

Consequently, it appears that the 2-alkyl-3-(4-hydroxybenzoyl) benzofurans in question, and especially benzarone, may be obtained with great ease and numerous advantages through the intermediacy of the molecular compounds of the invention.

These advantages are of particular interest when the starting 2-alkyl-3-(4-methoxybenzoyl)benzofurans are prepared in accordance with the preferred method of the invention, namely using a Friedel-Crafts reaction, with ferric chloride as a catalyst. In fact, it is thus possible to perform the various stages of preparation, namely the preparation of 2-alkyl-3-(4-methoxybenzoyl)benzofuran, the preparation of the molecular complexes and the demethylation, in the same aromatic hydrocarbon, for example toluene, avoiding thereby the isolation of the intermediate 2-alkyl-3-(4-methoxybenzoyl)benzofuran.

In accordance with another aspect, the invention relates to a process for preparing 2-alkyl-3-(4-hydroxybenzoyl)benzofurans involving the use of solutions containing the molecular complexes of the invention, process which comprises:

reacting a 2-alkylbenzofuran and a 4-methoxybenzoyl halide preferably the chloride, in an aromatic hydrocarbon, for instance toluene, at a temperature of between $-10°$ C. and room-temperature and in the presence of ferric chloride as a catalyst and then hydrolysing in the presence of a strong acid for instance hydrochloric acid to obtain a solution of corresponding 2-alkyl-3-(4-methoxybenzoyl)benzofuran, introducing, at a temperature below or equal to room-temperature, to 2 mols of aluminium chloride per mol of 2-alkyl-3-(4-methoxybenzoyl)benzofuran and pouring the solution so obtained into an aromatic hydrocarbon under reflux, for example toluene, hydrolysing the solution obtained in the presence of a strong acid for instance hydrochloric acid at a temperature not exceeding 75° C. to 80° C., to obtain the required 2-alkyl-3-(4-hydroxybenzoyl) benzofuran.

The 2-alkyl-3-(4-hydroxybenzoyl)benzofurans themselves may be used as synthesis intermediates to prepare, in particular, benziodarone, benzbromarone or amiodarone according to the known methods.

For example, benziodarone and benzbromarone may be obtained, respectively, by iodination or bromination of 2-ethyl-3-(4-hydroxybenzoyl) benzofuran by means of iodine or bromine, respectively, in a homogeneous phase and in the presence of a buffer solution of an alkaline metal acetate and acetic acid, and amiodarone may be prepared by iodination of 2-n-butyl-3-(4-hydroxybenzoyl)benzofuran, in a similar manner to that described hereabove to obtain 2-n-butyl-3-(3,5-diiodo-4-hydroxybenzoyl)benzofuran, followed by an etherification using 1 -diethylamino-2-chloroethane hydrochloride in the presence of a buffer solution containing an alkali metal carbonate and an alkali metal bicarbonate.

The following non limiting examples illustrate the invention:

EXAMPLE 1

Preparation of the 1:1 complex of aluminium chloride with 2-n-butyl-3-(4-methoxybenzoyl)benzofuran (4-methoxybenzoyl)benzofuran.

In 100 ml of anhydrous methylene chloride were dissolved 15 g (0.0373 mol) of 2-n-butyl-3-(4-methoxybenzoyl)benzofuran. The solution was cooled to $-10°$ C. while protected from moisture and 5 g (0.0373 mol) of anhydrous aluminium chloride were added to it rapidly, in a single portion. The whole solution was filtered to remove a few suspended impurities and was evaporated to dryness under reduced pressure (p =20 mm Hg; temperature <10° C.) and under nitrogen atmosphere dried over pumice moistened with sulphuric acid.

The honey-like product did not cristallize in the deep-freeze after 15 h at $-20°$ C. It was taken up twice with 50 ml of carbon tetrachloride and, on the second occasion, crystallization was observed after 48 h at $-20°$ C.

The crystals were separated off and dried in a stream of dry nitrogen at $-20°$ C. and were stored in the deep-freeze.

In this manner 14.8 g of a 1:1 complex of aluminium chloride with 2-n-butyl-3-(4-methoxybenzoyl)benzofuran were obtained in the form of a deep-yellow crystalline mass, which was relatively unstable and which hydrolysed rapidly.

Yield: 89.7%

M.p.: translucent at +25° C. completely melted at +40° C. irreversible.

Using the same method as before, the 1:1 complex of aluminium chloride with 2-ethyl-3-(4-methoxybenzoyl)-benzofuran was prepared.

EXAMPLE 2

Preparation of the 2:1 complex of aluminium chloride with 2-n-butyl-3-(4-hydroxybenzoyl)benzofuran In 300 ml of dry toluene were dissolved 30.8 g (0.1 mol) of 2-n-butyl-3-(4-methoxybenzoyl)benzofuran and the solution was cooled to -10° C. while protected from moisture. After this operation, 26.7 g (0.2 mol) of anhydrous aluminium chloride were added rapidly in a single portion. A solution containing the 1:1 complex of aluminium chloride with 2-n-butyl-3-(4-methoxybenzoyl)benzofuran was thus obtained and was poured into anhydrous toluene heated to reflux temperature. The reflux temperature was maintained for another hour, while toluene was distilled off.

At the end of the reaction, the reaction medium was gradually cooled. Crystallization began at about +40° C. After maintaining a temperature of +5° C. for 2 h, the solid was filtered off and the filter cake was dried in a vacuum oven at +55° C. in a stream of dry nitrogen.

In this manner 49 g of 2:1 complex of aluminium chloride with 2-n-butyl-3-(4-hydroxybenzoyl)benzofuran were obtained in the form of a finely divided yellowish powder.

M.p.: >300° C. with decomposition

I.R. spectrum: absence of free C=O band, associated C=O band

N.M.R. spectrum: very broad spectrum, absence of a —OCH$_3$ signal

Determination of aluminium (complexometry): 9.36–9.5–9.6% (theory: 9.63%).

The 2:1 complex of aluminium chloride with 2-ethyl-3-(4-hydroxybenzoyl)-benzofuran was prepared in the same manner as above.

EXAMPLE 3

Preparation of solutions containing the complexes of aluminium chloride with 2-n-butyl-3-(4-methoxy- and 4-hydroxybenzoyl)berzofurans (a) 2-n-Butyl-3(-4-methoxybenzoyl)benzofuran Into a reactor were introduced 520 g (600 ml) of toluene and 174 g (1 mol) of 2-n-butylbenzofuran. The mixture was heated to reflux, with stirring and the medium and the apparatus were dried by taking off a forerun, using a Dean Stark system. Approximately 35 g (about 40 ml) of toluene were removed by distillation in this manner. The reactor was cooled to room-temperature and 174 g (1.02 mol) of 4-methoxybenzoyl chloride were introduced rapidly in a single portion. The mixture was chilled to −10° C.±2° C. and 130 g (0.8 mol) of anhydrous ferric chloride were added, also rapidly and as a single portion.

The reaction medium was maintained at −10° C.±2° C. for 15 minutes and was then allowed to return to room-temperature. The mixture was kept stirred for 6 hours and was once again chilled to about 0° C. After this operation, 200 g of purified water were then added gradually, without exceeding 20° C.

After being kept at room-temperature for 30 minutes, the insoluble product (4-methoxybenzoic acid) was filtered off and was then rinsed on the filter with 90 g of toluene. The filtrates were collected in a separating funnel, the lower aqueous phase was separated off and the organic layer was washed with a solution of 30 g of 36%-hydrochloric acid in 200 g of purified water, and then with water until neutral. The organic phase was dried and the solvent was removed under vacuum until the mass reached a temperature of 80° C. under a residual pressure of about 50 mm Hg.

In this manner, about 308 g of 2-n-butyl-3-(4-methoxy-benzoyl)-benzofuran were obtained in crude form.

Yield: about 100%.

The 2-n-butyl-3-(4-methoxybenzoyl)benzofuran obtained by this method had, on average, the following contents of impurities identified by thin-layer chromatography.

| | |
|---|---|
| 2-n-Butylbenzofuran | ≦1.5% |
| 2-n-Butyl-6-(4-methoxybenzoyl)benzofuran/ 2-n-butyl-5-(4-methoxybenzoyl)benzofuran | ≦2% |

(b) Complexes of aluminium chloride with 2-n-butyl-3-(4-methoxy- and 4-hydroxybenzoyl)benzofurans Into a reactor fitted with devices for adding reactants, stirring and cooling, were introduced 308.3 g (1 mol) of 2-n-butyl-3-(4-methoxy-benzoyl)benzofuran in 625 g of toluene. After the mixture had been cooled to 0° C., 253.3 g (1.9 mol) of aluminium chloride were added with rapid stirring. In this manner, a solution containing the 1:1 complex of aluminium chloride with 2-n-butyl-3-(4-methoxybenzoyl)benzofuran was produced.

The toluene solution containing the 1:1 complex, prepared in this manner, was introduced into a second, identical reactor containing 493 g of anhydrous toluene heated to reflux temperature. While distilling off toluene (462 g) the reaction mixture was maintained under reflux for another hour after the addition was complete, which provoked the formation of the 2:1 complex of aluminium chloride with 2-n-butyl-3-(4-hydroxybenzoyl)benzofuran.

In this manner, a toluene solution of molecular complex of aluminium chloride with 2-n-butyl-3-(4-hydroxybenzoyl)benzofuran was obtained which was used as such.

EXAMPLE 4

Preparation of solutions containing the complexes of aluminium chloride with 2-n-butyl-3-(4-methoxy- and 4-hydroxybenzoyl)benzofurans (a) 2-n-Butyl-3-(4-methoxybenzoyl)benzofuran Into a reactor fitted with devices for stirring, adding reactants and with a condenser were introduced 174 g (1 mol) of 2-n-butylbenzofuran and 520 g of toluene. Traces of water were removed by azeotropic distillation. The mixture was cooled to 20° C. and 174 g (0.12 mol) of 4-methoxybenzoyl chloride were added rapidly. After cooling to −10° C., the medium was treated with 130 g of ferric chloride, added in a single portion. After 15 minutes at this temperature, the mixture was allowed to return to ambient temperature and was stirred for 6 hours at this temperature. The medium was hydrolysed by the addition of 200 ml of water, the temperature not being allowed to exceed 20° C. After 15 minutes at this temperature, an insoluble product (4-methoxybenzoic acid) was filtered off, the filter was washed with toluene, and the aqueous phase was separated off. The organic phase was washed with a solution of 30 g of 36%-hydrochloric acid in 200 ml of water, and then with water until neutral, and was then dried.

In this manner, a toluene solution containing about 308 g (about 100%) of 2-n-butyl-3-(4-methoxybenzoyl)-benzofuran was obtained and was used as such.

(b) Complexes of aluminium chloride with 2-n-butyl-3-(4-methoxy- and 4-hydroxybenzoyl)benzofurans A toluene solution of 308.3 g of crude 2-n-butyl-3-(4-methoxybenzoyl)benzofuran (1 mol, expressed as dry residue), as obtained in section (a) above, namely an approximately 30% strength solution, was introduced into a reactor.

With stirring and cooling to 0° C., 253.3 g (1.9 mol) of aluminium chloride were added rapidly and the mixture was allowed to return to room-temperature.

In this manner, a toluene solution containing the 1:1 complex of aluminium chloride with 2-n-butyl-3-(4-methoxybenzoyl)benzofuran was produced.

Into a second reactor, 493 g of toluene were introduced and were then heated to reflux with stirring so as to dry the apparatus and the solvent by azeotropy. While the medium was kept under reflux by heating, the solution containing the 1:1 complex, obtained above, was added over approximately 2.5±0.5 h. After rinsing with 138 g of anhydrous toluene, the mixture was kept refluxing briskly for 1 h while toluene was distilled off (462 g), which provoked the formation of the 2:1 complex of aluminium chloride with 2-n-butyl-3-(4-hydroxybenzoyl)benzofuran.

In this manner a toluene solution of molecular complex of aluminium chloride with 2-n-butyl-3-(4-hydroxybenzoyl)benzofuran was obtained which was used as such.

EXAMPLE 5

Preparation of solutions containing the complexes of aluminium chloride with 2-ethyl-3-(4-methoxy- and 4-hydroxybenzoyl)benzofurans (a) 2Ethyl-3-(4-methoxybenzoyl)benzofuran Into a reactor, 146.2 g (1 mol) of 2-ethylbenzofuran (99.8% assay) and 520 g (600 ml) of toluene were introduced. The medium was heated to reflux with stirring and was dried by taking off a forerun using a Dean Stark system. Approximately 35 g (about 40 ml) of toluene were distilled off in this manner. The reactor was cooled to room-temperature and 174 g (1.02 mol) of 4-methoxybenzoyl chloride (98% assay) were added rapidly as a single portion. The mixture was chilled to −10°+2° C. and 130 g (0.8 mol) of anhydrous ferric chloride were added rapidly in a single portion. The reaction medium was kept at this temperature for 15 minutes, and was then allowed to return to room-temperature for 6 hours. The mixture was then chilled to 0° C. and hydrolysed without exceeding 10° C. by gradual addition of 200 g of deionized water. The insoluble product (4-methoxybezoic acid) was filtered off and the aqueous phase was separated off. The organic phase was washed with a previously prepared solution of 200 g of deionized water and of 30 g of 36%-hydrochloric acid, and then with deionized water until the pH of the runnings was 5 to 6. Approximately 500 g of toluene were distilled off under reduced pressure (temperature of the mass:80° C., residual pressure:80 to 100 mm Hg), and then the vacuum was broken with nitrogen and 280 g of n-heptane were added. Crystallization was performed at room-temperature, and the material was filtered off after 2 h of chilling to −5° to −10° C., and was then dried to constant weight in a ventilated oven at 50° C.

In this manner about 260 g of crude 2-ethyl-3-(4-methoxybenzoyl)-benzofuran were obtained.
Yield:approximately 93%
M.P.:81° C.

(b) Complexes of aluminium chloride with 2-ethyl-3-(4-methoxy- and 4-hydroxybenzoyl)benzofurans Into a first reactor, 280.3 g (1 mol) of crystallized 2-ethyl-3-(4-methoxybenzoyl)benzofuran and 588 g of toluene were introduced. The solid was dissolved by heating, with stirring, the reactants were dried azeotropically and the solution obtained was cooled to 10° C.

Into a second perfectly dry reactor, 253 g of anhydrous toluene were introduced followed, with cooling, by 241 g (1.8 mol) of anhydrous aluminium chloride. The temperature of the mass was adjusted to 0°±5° C. and the toluene solution of 2-ethyl-3-(4-methoxybezoyl)benzofuran prepared in the first reactor was added. The addition took approximately 90 minutes, with external cooling so as not to exceed 15° C. The solution produced in this manner, containing the 1:1 complex of aluminium chloride with 2-ethyl-3-(4-methoxybenzoyl)benzofuran was then kept at a temperature below or equal to 15° C.

Into the first reactor 356 g of anhydrous toluene were introduced and then stirred and placed under a residual pressure of 300–350 mm Hg, before the toluene was heated to reflux (mass temperature:84°±1° C.). The vacuum and the temperature were stabilized, the system was set for distillation and then a gradual addition of the solution in the second reactor, containing the complex, was started (total addition time of complex:4 to 5 h; toluene-containing distillate:about 1400 g). The second reactor was rinsed with 48 g of anhydrous toluene and the mass was heated to 100° C. while the reduced pressure in the reactor was gradually lowered (toluene-containing distillate: approximately 105 g), which provoked the formation of the 2:1 complex of aluminium chloride with 2-ethyl-3-(4-hydroxybenzoyl)benzofuran.

In this manner, a toluene solution of a molecular complex of aluminium chloride with 2-ethyl-3-(4-hydroxybenzoyl)benzofuran was obtained.

EXAMPLE 6

Preparation of solutions containing the complexes of aluminium chloride with 2-ethyl-3-(4-methoxy- and 4-hydroxybenzoyl)benzofurans (a) 2-Ethyl-3-(4-methoxybenzoyl)benzofuran.

Into a reactor were introduced 109.6 g (0.75 mol) of 2-ethylbenzofuran and 388 g of toluene. The medium was dried azeotropically (tolune-containing distillate:approximately 27 g). The reactor was cooled to 20° C. and 130 g of 4-methoxybenzoyl chloride were added rapidly. The mixture was cooled to −10°+2° C. and 97 g of anhydrous ferric chloride were added rapidly. The mixture was kept at a low temperature for 30 minutes, and was then allowed to return to a temperature of 20°±3° C., which was maintained for 6 h. Hydrolysis was carried out by adding 150 g of deionized water, the mass was heated to 40°±2° C. and the aqueous phase was separated off. The organic phase was washed, at 40°+2° C., for 30 minutes with a previously prepared solution of 150 g of deionized water and 225 g of 36%-hydrochloric acid. It was separated off and still washed at 40° C., with 3 to 5 portions each of 200 g of deionized water until the spent wash had a pH≧5. The toluene solution was then treated with 45 g of activated charcoal, heated to reflux and water was removed azeotropically. The solution was filtered hot to remove the impurities, rinsed, still hot, with 68 g of toluene, and the filtrates were collected.

In this manner, a toluene solution containing about 190 g (approximately 90% of 2-ethyl-3-(4-methoxybenzoyl)benzofuran was obtained and used as such.

(b) Complexes of aluminium chloride with 2-ethyl-3-(4-methoxy- and 4-hydroxybenzoyl)benzofurans A toluene solution of 280.3 g of crude 2-ethyl-3-(4-methoxybenzoyl) benzofuran (1 mol, expressed as dry residue), as obtained in section (a) above, namely a solution of about 30% strength, was introduced into a first, perfectly dry, reactor. This was cooled to a temperature below or equal to 5° C. and 266 g (2 mols) of anhydrous aluminium chloride were added rapidly under stirring and in a single portion, to form a solution containing the 1:1 complex aluminium chloride with 2-ethyl-3-(4-methoxybenzoyl)benzofuran. This solution, containing the complex, was kept stirred for 30 minutes at a temperature of less than 30° C. and protected from moisture.

In a second reactor, 348 g (400 ml) of anhydrous toluene were heated to reflux and then, under reflux, the toluene solution containing the complex and obtained previously was added over 1.5 to 2 h. As soon as the addition was complete, the apparatus was set to distillation (toluene-containing distillate:approximately 400 ml) and was again changed over to total reflux for 1 h, which provoked the formation of a 2:1 complex of aluminium chloride with 2-ethyl-3-(4-hydroxybenzoyl)benzofuran.

In this manner, a toluene solution of molecular complex of aluminium chloride with 2-ethyl-3-(4-hydroxybenzoyl)benzofuran was obtained and used as such.

EXAMPLE 7

Preparation of solutions containing the complexes of aluminium chloride with 2-ethyl-3-(4-methoxy- and 4-hydroxybenzoyl)benzofurans Into a perfectly dry reactor, were introduced 244 g (280 ml) of anhydrous toluene followed by 266 g (2 mols) of anhydrous aluminium chloride, added rapidly as a single portion. While the mixture was stirred and cooled not to exceed 20° C., a toluene solution of 280.3 g of crude 2-ethyl-3-(4-methoxybenzoyl)benzofuran (1 mol, expressed as dry residue), as obtained in Example 6(a), namely a solution of about 30% strength was added gradually. The mixture was heated gradually to reflux over 1 to 1.5h, and was then maintained at this temperature for 1 h.

A toluene solution of 2:1 molecular complex of aluminium chloride with 2-ethyl-3-(4-hydroxybenzoyl)-benzofuran was so obtained.

Using the same method as that described above, but starting from a toluene solution of 308.3 g of 2-n-butyl-3-(4-methoxybenzoyl) benzofuran (1 mol, expressed as dry residue), a toluene solution of 2:1 molecular complex of aluminium chloride with 2-n-butyl-3-(4-hydroxybenzoyl)benzofuran was obtained.

The following Examples illustrate the preparation of 3-benzoylbenzofuran derivatives and especially benzarone, benziodarone, benzbromarone and amiodarone, from the molecular complexes of formula I of the invention.

EXAMPLE I

Preparation of 2-n-butyl-3-(4-hydroxybenzoyl)benzofuran

The toluene solution of molecular complex obtained in Example 3b), cooled to about 75° C., was poured, under stirring, into a solution of 46.2 g of 36%-hydrochloric acid in 600 g of water. After 15 minutes the aqueous phase was separated off and the organic phase was washed to neutrality with water. The toluene phase was dried by azeotropic distillation of water (distillation of 92 g of toluene) and was decolorized by a treatment with bleaching clay at 80° C. After filtering and rinsing the filter with toluene, the filtrate was cooled to about −5° C. to −10° C. and the required product was isolated by filtration.

In this way, 253 g of crude 2-n-butyl-3-(4-hydroxybenzoyl)benzofuran were obtained.

Yield:86%

M.P.:119° C.

A thin-layer chromatogram showed that this compound was free from 2-(4-hydroxyphenyl)benzofuran.

EXAMPLE II

Preparation of 2-ethyl-3-(4-hydroxybenzoyl)benzofuran

The toluene solution of molecular complex, obtained in Example 5(b), cooled beforehand to 75° C., was added over 1 to 2 h, without exceeding 80° C., to a solution of 108 g of 36%-hydrochloric acid in 530 g of deionized water. The lower aqueous phase was separated off at 75°-80° C. and the organic layer was washed at this temperature with 3 portions, each of 280 g, of deionized water. After the last separation, the medium was dried azeotropically at normal pressure using a Dean Stark system until a head temperature of 108°-110° C. was obtained. The medium was then cooled to 80° C., treated with 11 g of bleaching clay for 15 min., filtered and rinsed hot with 60 g of toluene. The filtrates were collected, crystallized by gradual cooling, and chilled to −5° C. for 2 h before filtration. The precipitate was rinsed with two portions, each of 120 g, of chilled anhydrous toluene and was dried to constant weight in a vacuum oven at 50° C.

In this manner, 233 g of crude 2-ethyl-3-(4-hydroxybenzoyl) benzofuran, or benzarone, were obtained. Yield:83±3% [based on 2-ethyl-3-(4-methoxybenzoyl)-benzofuran].

EXAMPLE III

Preparation of 2-ethyl-3-(4-hydroxybenzoyl)benzofuran

The toluene solution of molecular complex, obtained in Example 6 (b) cooled beforehand to 70°±5° C., was introduced, with stirring, into 600 g of deionized water. The mixture was rapidly reheated to reflux and was then cooled to 70°±5° C. to separate the lower aqueous layer. The organic layer was washed, still at 70°±5° C., with a solution of 42 g of 36%-hydrochloric acid in 266 g of deionized water, and then with 4 portions, each of 266 g, of deionized water to neutrality. The organic layer was dried azeotropically at normal pressure (toluene/water distillate:approximately 244 g or 280 ml) and the medium obtained was treated with 84 g of bleaching clay for 15 minutes at 80° C., filtered and rinsed hot with 56 g (65 ml) of toluene. The filtrates were collected and crystallization was induced by cooling. The product was filtered off after 2 h at −5° to −10° C., rinsed with 168 g (195 ml) of chilled toluene and dried to constant weight in a ventilated oven at 60° C.

In this manner, about 234 g of crude 2-ethyl-3-(4-hydroxybenzoyl) benzofuran, or benzarone, were obtained.

Yield:about 88% [based on the dry residue expressed as 2-ethyl-3-(4-methoxybenzoyl)benzofuran].

EXAMPLE IV

Preparation of
2-ethyl-3-(4-hydroxybenzoyl)benzofuran

The toluene solution of molecular complex, obtained in Example 7, cooled beforehand to 80°±5° C., was introduced under stirring, into 600 g of deionized water. The mixture was reheated rapidly to reflux and then cooled to 70°±5° C. to separate off the lower aqueous layer. The organic layer was washed, still at 70°±5° C., with a solution of 42 g of 36%-hydrochloric acid in 266 g of deionized water, and then with 4 portions, each of 266 g, of deionized water, to neutrality. The organic layer was dried azeotropically at normal pressure (toluene/water distillate:approximately 244 g or 280 ml) and the medium obtained was treated with 84 g of bleaching clay for 15 minutes at 80° C., filtered and rinsed hot with 56 g (65 ml) of toluene. The filtrates were collected and crystallization was induced by cooling. The precipitate was filtered off after 2 h at −5 to −10° C., rinsed with 168 g (195 ml) of chilled toluene and dried to constant weight in a ventilated oven at 60° C.

In this manner, about 266 g of crude 2-ethyl-3-(4-hydroxybenzoyl) benzofuran, or benzarone, were obtained.

Yield: 88±1% [based on the dry residue, expressed as 2-ethyl-3-(4-methoxybenzoyl)benzofuran].

M.P.:126° C.

Using the same method as that described above, but starting from the toluene solution of molecular complex obtained in Example 8, about 216 g of crude 2-ethyl-3-(4-methoxybenzoyl)benzofuran were obtained, representing a yield of 81±1% based on the dry extract, expressed as 2-ethyl-3-(4-methoxybenzoyl)benzofuran.

M.P.:125° C.

EXAMPLE V

Preparation of
2-n-butyl-3-(3,5-diiodo-β-diethylaminoethoxybenzoyl) benzofuran hydrochloride (a) 2-n-Butyl-3-(4-hydroxybenzoyl)benzofuran The toluene solution of molecular complex obtained in Example 4(b) was hydrolysed, under stirring and at a temperature below or equal to 75° C., by the addition of a solution of 46.2 g of 36%-hydrochloric acid in 600 g of distilled water. The apparatus was rinsed with 123 g of toluene which were then added to the hydrolysis medium. After 15 minutes at a temperature of 70° C. within the material, the organic layer was separated off and washed at 70° C. with portions each of 308 g of purified water, until neutral. The organic layer was dried azeotropically while approximately 92 g of toluene were distilled off. The medium was treated at 80° C. with 12.3 g of bleaching clay, filtered and rinsed with 92 g of hot toluene. The filtrates were collected, cooled to 35° C. and, after waiting for the crystallization to become well-initiated chilled to −5° to −10° C. This temperature was maintained for 2 h and the precipitate formed was filtered off, rinsed with 200 g of chilled toluene, and dried to constant weight in a ventilated oven at 60° C.

In this manner, about 253 g of crude 2-n-butyl-3-(4-hydroxybenzoyl)-benzofuran were obtained.

Yield:about 86% (based on 2-n-butylbenzofuran).

(b)
2-n-Butyl-3-(3,5-diiodo-4-hydroxybenzoyl)benzofuran

Into a 4-1 reactor were introduced 540 g of methanol and, while stirring were added in succession, 300 g (2.4 mols) of sodium acetate trihydrate, 286 g of iodine and 424 g of moist recovered iodine (2.3 mols in all). The reaction medium was warmed to 30° to 35° C., and 294 g (1 mol) of 2-n-butyl-3-(4-hydroxybenzoyl)benzofuran were added in a single portion. After rinsing with 60 g of methanol, the mixture was heated to reflux over 30 to 45 minutes (bulk temperature:70° to 74° C.). Heating was interrupted and a previously prepared solution of 90 g (2.2 mols) of sodium hydroxide flakes in 400 g of purified water was added over approximately 10 minutes. The exothermicity of the reaction maintained the liquid refluxing (76°–77° C. in the bulk) during the addition period. The mixture was kept refluxed for 2 h and then the apparatus was modified for distillation at atmospheric pressure. An aqueous solution of 320 g of sodium bisulphite (35°Bé) was added over approximately 20 minutes and distillation was continued until a bulk temperature of 97° to 100° C. was reached (head temperature:87° C.). About 800 ml (approximately 680 g) of solvent were distilled off in this manner. The residue was cooled to 75° to 80° C. using a water bath and the following were added in succession, in this order: 200 g of purified water, 215 g of 36%-hydrochloric acid and 1600 g of toluene. The mixture was heated to reflux for 10 minutes (bulk temperature: 84° C., evolution of sulphur dioxide) and the lower aqueous phase was separated off. The toluene layer was washed at 75° to 80° C. successively with 400 g of purified water, 100 g of an aqueous solution of sodium bisulphite and 2 portions, each of 400 g, of purified water. The last wash was separated off as well as possible and the organic phase was treated with 22 g of activated charcoal for 30 minutes under reflux, filtered hot and rinsed with 380 g of hot toluene. The filtrates were then combined.

A toluene solution of 2-n-butyl-3-(3,5-diiodo-4-hydroxybenzoyl) benzofuran was so obtained which was used as such.

Using the same method as that described above, but starting from 266.3 g (1 mol) of 2-ethyl-3-(4-hydroxybenzoyl)benzofuran, 2-ethyl-3-(3,5-diiodo-4-hydroxybenzoyl)benzofuran or benziodarone, was obtained after removal of the toluene by distillation.

Similarly, by starting from 266.3 g (1 mol) of 2-ethyl-3-(4-hydroxybenzoyl)benzofuran and bromine, 2-ethyl-3-(3,5-diiodo-4-hydroxybenzoyl)benzofuran, or benzbromarone, was obtained after removal of the toluene by distillation.

(c) 2-n-Butyl-3-(3,5-diiodo-4-6β -diethylaminoethoxybenzoyl)benzofuran

The toluene solution of 2-n-butyl-3-(3,5-diiodo-4 hydroxybenzoyl) benzofuran obtained in Section (b) was introduced into a reactor, together with 800 g of purified water and 177.3 g (1.03 mol) of 1-diethylamino-2-chloroethane hydrochloride. The reaction medium was heated to 40°±2° C. while being stirred and this temperature was maintained for 15 minutes. While the release of carbon dioxide was kept under control, 416 g (3 mols) of anhydrous potassium carbonate were then slowly sprinkled. The temperature was raised gradually so to reach reflux over 1 hour and the mixture was maintained at this temperature for 3 h. The saline aqueous layer was separated off at 75°±5° C. and the toluene layer was washed at this temperature with 4 portions, each of 800 g, of purified water. The toluene solution was treated at a temperature of 60° C. with 20.5 g of activated charcoal, which is filtered off, rinsed with approximately 220 g of toluene, and the filtrates were collected.

In this manner, a toluene solution of 2-n-butyl-3-(3,5-diiodo-4-β-diethylaminoethoxybenzoyl)benzofuran was obtained in base form, or amiodarone.

(d) 2-n-Butyl-3-(3,5-diiodo-4-β-diethylaminoethoxybenzoyl)benzofuranhydrochloride The solution of 2-n-butyl-3-(3,5-diiodo-4-β-diethylaminoethoxybenzoyl)benzofuran obtained in Section (c) was adjusted to 60° C. and 38.5 g of hydrogen chloride gas were introduced through a dip-pipe over 45 min. The temperature of the bulk was allowed to increase as a result of the exothermicity of the reaction, but without exceeding 75° C.

The strongly acid pH was checked at the end of the addition and after 30 minutes' contact at 70°±5° C. A water-pump vacuum was applied gradually and approximately 400 ml of a toluene/water/hydrochloric acid mixture were distilled off (end of distillation:residual pressure ≦150 mm; bulk temperature ≦75° C.). Crystallization took place on slow stirring in a water bath for approximately 8 hours and the precipitate was filtered off at 10° to 15° C., rinsed with 4 portions, each of 180 ml, of filtered toluene, and dried to constant weight in a ventilated oven at 60° C.

In this manner, about 647.5 g of 2-n-butyl-3-(3,5-diiodo-4-β-diethylaminoethoxybenzoyl)benzofuran hydrochloride, or amiodarone hydrochloride were obtained.

Yield:approximately 95% [based on 2-n-butyl-3-(4-hydroxybenzoyl) benzofuran].

We claim:

1. In a process for preparing 3-(4-hydroxybenzoyl)-benzofuran having a formula:

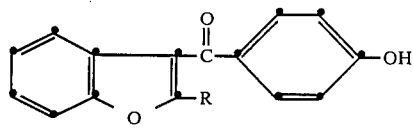

in which R represents a $C_{1-4}$ alkyl group which comprises reacting a benzofuran derivative having a formula:

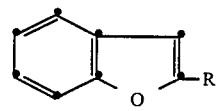

in which R has the same meaning as above, with a 4-methoxybenzoyl halide in an aromatic hydrocarbon, at a temperature of between −10° C. and room-temperature and in the presence of ferric chloride as a catalyst, hydrolysing the reaction product so formed, in the presence of a strong acid, to obtain a solution of the corresponding 2-alkyl-3-(4-methoxybenzoyl)benzofuran and subsequently demethylating the said 2-alkyl-3-(4-methoxybenzoyl)-benzofuran in crude form so obtained using aluminum chloride, wherein the improvement comprises introducing in the solution of 2-alkyl-3-(4-methoxybenzoyl)benzofuran at a temperature below or equal to room-temperature, 1.8 to 2 mols of aluminum chloride per mol of 2-alkyl-3-(4-methoxybenzoyl)benzofuran to form a 1:1 complex having a formula:

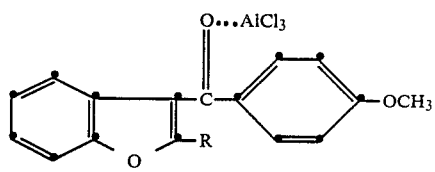

in which R has the same meaning as above, gradually pouring the solution, which contains the 1:1 complex so obtained into an aromatic hydrocarbon under reflux to form the 2:1 complex having a formula:

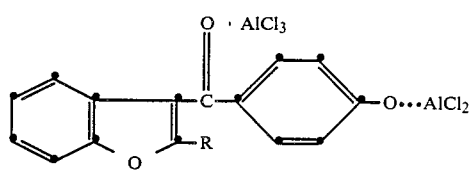

in which R has the same meaning as above the hydrolysing, the solution which contains the 2:1 complex so obtained, the presence of a strong acid at a temperature nor exceeding 75° C. to 80° C. to provide the required 2-alkyl-3-(4-hydroxybenzoyl)benzofuran.

2. A process according to claim 1 in which R represents an ethyl group.

3. A process according to claim 1 in which R represents a n-butyl group.

4. A process according to claim 1 in which the aromatic hydrocarbon is toluene.

5. A process according to claim 2 in which the aromatic hydrocarbon is toluene.

6. A process according to claim 3 in which the aromatic hydrocarbon is toluene.

* * * * *